(12) United States Patent
Tseng et al.

(10) Patent No.: US 9,999,645 B2
(45) Date of Patent: *Jun. 19, 2018

(54) METHOD OF MAKING LONGAN SEED EXTRACT

(71) Applicant: JOBEN BIO-MEDICAL CO., LTD., Pingtung County (TW)

(72) Inventors: Huang-Chung Tseng, Kaohsiung County (TW); Chien-Wei Hou, Kaohsiung County (TW)

(73) Assignee: JOBEN BIO-MEDICAL CO., LTD., Pingtung County (TW)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/327,393

(22) Filed: Jul. 9, 2014

(65) Prior Publication Data

US 2015/0079204 A1  Mar. 19, 2015

Related U.S. Application Data

(62) Division of application No. 13/382,907, filed as application No. PCT/CN2009/072687 on Jul. 8, 2009, now abandoned.

(51) Int. Cl.
*A61K 8/00* (2006.01)
*A61K 36/77* (2006.01)

(52) U.S. Cl.
CPC .................. *A61K 36/77* (2013.01)

(58) Field of Classification Search
None
See application file for complete search history.

(56) References Cited

U.S. PATENT DOCUMENTS

| 5,718,897 | A | 2/1998 | Herman |
| 2007/0014882 | A1 | 1/2007 | Feldman |
| 2007/0048234 | A1* | 3/2007 | Waugh .................. A61K 31/192 424/61 |

FOREIGN PATENT DOCUMENTS

| JP | H10-212244 A | 8/1998 |
| JP | 2001247471 | 9/2001 |
| JP | 2002145732 | 5/2002 |
| JP | 2005-343823 | 12/2005 |
| JP | 2005-343823 A | 12/2005 |
| JP | 2005343823 | 12/2005 |
| JP | 2005343823 A * | 12/2005 |
| JP | 2006-43204 A | 2/2006 |
| JP | 2006-342095 | 12/2006 |
| JP | 2006342095 | 12/2006 |
| WO | 2008129070 | 10/2008 |

OTHER PUBLICATIONS

Longan 2015 https://en.wikipedia.org/wiki/Longan.*
"Isolation and structure elucidation of phenolic compounds from longan (Dimocarpus longan Lour.) seed by high-performance liquid chromatography-electrospray ionization mass spectrometry." Journal of Chromatography A, 1085 (2005): p. 270-277.
"Evaluation of free radical scavenging and antityrosinase activities of standardized longan fruit extract." Food and Chemical Toxicology, (45)2007, p. 328-336.
"Xanthine oxidase inhibitors from the leaves of Lagerstroemia speciosa (L.) Pers." Journal of Ethnopharmacology, (93)2004, vol. 93, p. 391-395.
Traditional Chinese Medicine Dictionary, Shogakukan Inc.,1998 vol. 4, p. 2679 (without translation).
Office Action dated Jun. 7, 2013 by JIPO for the corresponding Japanese Patent Application No. 2012-518722.
Office Action dated Jul. 23, 2013 by JIPO for the corresponding Japanese Patent Application No. 2012-518722.
English Abstracts of JP 2006342095A, JP 2001247471A, JP 2002145732A and JP 2005343823A.
Office action and search report dated Jul. 26, 2012 for corresponding Taiwan application 098132865. Corresponds to U.S. Appl. No. 13/382,907.
Soong, Yeah-Yeah et al. Quantification of gallic acid and ellagic acid from longan (Dimocarpus longan Lour.) seed and mango (*Mangifera indica* L.) kernel and their effects on antioxidant activity, Food Chemistry, 2006, pp. 524-530, vol. 97.
Liao, Chen-Wei et al., "Application of On-line Antioxidative Activity Assay in Bioresource Materials", Master dissertation, National Chiayi University, Department of Biological Resources 2007.
English abstract translation of "Application of On-line Antioxidative Activity Assay in Bioresource Materials".
http://www.pabp.gov.tw/areabus/libA/a0305AppCom_01_051.asp.
Masuoka, Noriyoshi et al., Xanthine oxidase inhibitory activity of alkyl gallates, Molecular Nutrition and Food Research 2006;50(8):725-731.
Rejection dated Nov. 29, 2012 for corresponding Taiwan application 098132865.
Office action dated Mar. 27, 2014 for corresponding Taiwan application 098132865.
Office action dated Jan. 25, 2013 for corresponding China application 200980160302.2.
Chen Yingfeng et al., "Optimization of Extraction Conditions of Flavonoids from Longan Seed", Guangdong Chemical Industry 2009; 36(2):76-77, 89.
Office action dated Aug. 21, 2013 for corresponding China application 200980160302.2.
Rejection dated Apr. 8, 2014 corresponding China application 200980160302.2.
Office action dated Aug. 18, 2015 for the corresponding Chinese, P.R.C. Patent Application No. 201410387909.7.

(Continued)

*Primary Examiner* — Terry A McKelvey
*Assistant Examiner* — Catheryne Chen
(74) *Attorney, Agent, or Firm* — WPAT, P.C., Intellectual Property Attorneys; Anthony King

(57) ABSTRACT

A method of making longan seed extract is provided with choosing an extraction solvent; heating the extraction solvent to a first predetermined temperature; adding pulverized longan seed to the extraction solvent to prepare a solution; maintaining the solution at a second temperature for a predetermined period of time to obtain an extracted substance; filtering the extracted substance; and drying and cooling the filtered extracted substance to produce an extract.

4 Claims, 12 Drawing Sheets

(56) References Cited

OTHER PUBLICATIONS

Search Report dated Aug. 18, 2015 for the corresponding Chinese, P.R.C. Patent Application No. 201410387909.7.
English translation of the Search Report dated Aug. 18, 2015 for the corresponding Chinese, P.R.C. Patent Application No. 201410387909.7.
Chen Yingfeng et. al., "Optimization of Extraction Conditions of Flavonoids from Longan Seed", Guangdong Chemical Industry 36(2), 2009.
English abstract translation of "Optimization of Extraction Conditions of Flavonoids from Longan Seed".
Office action dated Feb. 19, 2016 for the corresponding China Patent Application No. 201410387867.7.
Search report dated Feb. 19, 2016 for the corresponding China Patent Application No. 201410387867.7.
English translation of the search report dated Feb. 19, 2016 for the corresponding China Patent Application No. 201410387867.7.
Chen, Yingfeng et al. "Optimization of Extraction Conditions of Flavonoids from Longan Seed", Guangdong Chemical Industry; vol. 36, Total No. 190, pp. 76-77, 89.
English abstract translation of Chen, Yingfeng et al. "Optimization of Extraction Conditions of Flavonoids from Longan Seed", Guangdong Chemical Industry; vol. 36, Total No. 190, pp. 76-77, 89.
Office action dated Sep. 15, 2015 for the corresponding Japanese Patent Application No. 2014-222599.
English translation of the office action dated Sep. 15, 2015 for the corresponding Japanese Patent Application No. 2014-222599.
Chuyaku Daijiten (Encyclopedia of Chinese Herbal Medicine), Shogakukan Inc., 1998, vol. 4, p. 2679.
JPH 10-212244 A corresponds to U.S. Pat. No. 5,718,897.
Soong, Yean Yean et al., Isolation and structure elucidation of phenolic compounds from longan (Dimocarpus longan Lour.) seed by high-performance liquid chromatography-electrospray ionization mass spectrometry, Journal of Chromatography A, 2005, vol. 1085, No. 2, -. 270-277.
Rangkadilok, Nuchanart et al., Evaluation of free radical scavenging and antityrosinase activities of standardized longan fruit extract, Food and Chemical Toxicology, 2007, vol. 45, No. 2, p. 328-336.
English abstract of JP 2006-43204 A.
Office action dated Sep. 16, 2015 for the corresponding Japanese Patent Application No. 2014-222712.
English translation of the Office action dated Sep. 16, 2015 for the corresponding Japanese Patent Application No. 2014-222712.
English abstract translation of JP 2005-343823 A.
Abstracts of Papers American Chemical Society, 2007, vol. 234, pp. 176-AGFD.
Office action dated May 6, 2016 for the corresponding Taiwan Patent Application No. 103125606.
Search report dated May 6, 2016 for the corresponding Taiwan Patent Application No. 103125606.
English translation of the search report dated May 6, 2016 for the corresponding Taiwan Patent Application No. 103125606.
English abstract translation of JP 2005-343823.
Soong, Yean-Yean et al., Quantification of gallic acid and ellagic acid from longan (Dimocarpus longan Lour.) seed and mango (*Mangifera indica* L.) kernel and their effects on antioxidant activity, Food Chemistry 97 (2006) pp. 524-530.
Office action and search report dated Jun. 15, 2016 for the corresponding German Patent Application No. 112009005041.7.
English translation of the Office action and search report dated Jun. 15, 2016 for the corresponding German Patent Application No. 112009005041.7.
JP 2005-343823 A WPI-summary and computer translation.
Soong, Y. Y. u. Barlow, Ph. J.: Isolation and structure elucidation of phenolic compounds from longan (Dimocarpus longan Lour.) seed by high-performance liquig chromatography-electrospray ionization mass spectrometry. In: J. Chromat. A, 2005, vol. 1085, S. 270-277.

\* cited by examiner

Corilagin

Gallic acid

Ellagic acid

| equipment | Agilent 1100 | | | | | | | |
|---|---|---|---|---|---|---|---|---|
| chromatography column | Atlantis®T3 5μm 4.6 X 10 mm, Waters | | | | | | | |
| pre-column | Cosmosil 5C18-AR-II 4.6 X 10 mm, Nacalai Tesque | | | | | | | |
| temperature | 25°C | | | | | | | |
| flow rate | 1.0 ml/min | | | | | | | |
| wavelength | UV 270 nm | | | | | | | |
| volume | 10 μl | | | | | | | |
| time(mintue) | 0 | 5 | 15 | 30 | 45 | 60 | 75 | 85 |
| 0.1% $H_3PO_4$ (%) | 98 | 97 | 97 | 87 | 86 | 81 | 79 | 0 |
| Acetonitrile, % | 2 | 3 | 3 | 13 | 14 | 19 | 21 | 100 |

FIG. 1B

| | IL-1β (ng/L) original | IL-1β (ng/L) after stress |
|---|---|---|
| control group | 119±12 | 117±22 |
| longan seed extract (7d) + LPS (24h) | 131±20 | 212±15 |
| longan seed extract (7d) + LPS (48h) | 102±16 | 213±19 |
| LPS (24h) + longan seed extract A | 116±14 | 212±18 |
| LPS (24h) + longan seed extract B | 104±17 | 190±20 |
| LPS (24h) + longan seed extract | 125±11 | 207±13 |
| LPS (48h) + longan seed extract | 110±16 | 211±10 |
| LPS (24h) | 111±20 | 209±9 |
| longan seed extract | 124±8 | 198±9 |

| | TNF-α (ng/L) original | IL-α (ng/L) after stress |
|---|---|---|
| control group | 549±37 | 527±22 |
| longan seed extract (7d) + LPS (24h) | 551±25 | 581±34 |
| longan seed extract (7d) + LPS (48h) | 547±30 | 633±28 |
| LPS (24h) + longan seed extract A | 586±22 | 744±41 |
| LPS (24h) + longan seed extract B | 564±31 | 753±33 |
| LPS (24h) + longan seed extract | 535±28 | 737±34 |
| LPS (48h) + longan seed extract | 599±33 | 741±35 |
| LPS (24h) | 531±31 | 769±35 |
| longan seed extract | 554±27 | 687±31 |

| time | Uric acid concentrations of control group | Uric acid concentrations of treatment group | Uric acid concentrations of longan seed extract group |
|---|---|---|---|
| 0-hour | 7.3±1.5mg/dl | 8.8±1.2mg/dl | 8.2±1.7mg/dl |
| 1-hour | 7.6±1.6mg/dl | 40.6±12.1mg/dl | 27.7±7.3mg/dl |

| sample | xanthine oxidase | solution of water and longan seed extract | solution 20% ethanol and longan seed extract | solution 50% ethanol and longan seed extract | solution 95% ethanol and longan seed extract |
|---|---|---|---|---|---|
| ppm | 5 | 50 | 50 | 50 | 50 |
| inhibition ratio (%) | 83 | 12 | 36 | 60 | 44 |

FIG. 5B

| | control group | 14 days | 28 days | 28 days |
|---|---|---|---|---|
| Number of rats | 8 | 10 | 10 | 10 |
| Original weight | 19.2±1.8 | 19.6±1.1 | 19.1±1.5 | 19.5±0.8 |
| Final weight | 19.2±1.8 | 19.2±1.8 | 19.2±1.8 | 25.9±1.07 |
| Oral Sample | 0 | 15g/kg | 1g/kg | 3 g/kg |
| Creatinine | 0.395±0.15 | 0.435±0.07 | 0.51±0.084 | 29.9±14.8 |
| GOT | 30.2±15.1 | 32.88±15.6 | 38.9±6.2 | 29.9±14.8 |
| GPT | 8.27±5.54 | 14.95±10.1 | 7.8±3.8 | 9.44±3.29 |
| Albumin | 2.8±1.37 | 2.75±1.08 | 2.63±1.64 | 2.57±0.8 |
| Globulin | 2.5±1.12 | 2.55±1.5 | 3.3±1.79 | 2.84±0.68 |

| | E. coli/plate | | Staphylococcus aureus/plate | |
|---|---|---|---|---|
| Test Times | Control group | Treatment group | Control group | Treatment group |
| 1st | 232 | 152 | 218 | 149 |
| 2nd | 121 | 82 | 239 | 134 |
| 3rd | 169 | 94 | 153 | 99 |
| avg±variance | 174±38 | 109±28 | 203±45 | 127±26 |

| | Propionibacterium acne/plate | |
|---|---|---|
| Test Times | Control group | Treatment group |
| 1st | 76 | 44 |
| 2nd | 47 | 19 |
| 3rd | 65 | 22 |
| avg±variance | 65±15 | 28±14 |

| | Trichophyton rubrum/plate | |
|---|---|---|
| Test Times | Control group | Treatment group |
| 1st | 176 | 128 |
| 2nd | 136 | 93 |
| 3rd | 182 | 133 |
| avg±variance | 165±25 | 118±22 |

| Dose (v/v%) | Times of growth |
|---|---|
| 0 | 1±0.060 |
| 1.25 | 0.98±0.075394 |
| 2.5 | 1.26±0.059782 |
| 5 | 1.27±0.090245 |
| 10 | 1.50±0.119184* |

FIG. 10

| Dose (v/v%) | CI (pg/ml) | CVI (pg/ml) | FN (pg/ml) |
|---|---|---|---|
| 0 | 144.8±14.61 | 150.1±33.47 | 53.5±8.96 |
| 5 | 84.9±7.54 | 73.6±23.57 | 80.9±11.31 |
| 10 | 269.8±36.77* | 171.1±3.77 | 141.1±1.89* |

FIG. 11

METHOD OF MAKING LONGAN SEED EXTRACT

CROSS REFERENCE TO RELATED APPLICATIONS

This nonprovisional utility application is a divisional application of and claims the benefit under 35 U.S.C. § 120 to co-pending U.S. application Ser. No. 13/382,907 filed Mar. 8, 2012, all of which are incorporated, in their entirety, by this reference.

BACKGROUND OF THE INVENTION

1. Field of the Invention

The invention relates to extraction techniques and more particularly to a method of making longan seed extract.

2. Description of the Related Art (1) Inflammation is part of the complex biological response of vascular tissues to harmful stimuli, such as pathogens, damaged cells, or irritants. Inflammation is a protective attempt by the organism to remove the injurious stimuli and to initiate the healing process. Inflammation is not a synonym for infection, even in cases where inflammation is caused by infection. Although infection is caused by a microorganism, inflammation is one of the responses of the organism to the pathogen. However, inflammation is a stereotyped response, and therefore it is considered as a mechanism of innate immunity. Contents of inflammation comprise nitric oxide (NO), tumor necrosis factor (TNF), interleukin (IL), granulocyte colony stimulating factor (G-CSF), monocyte colony stimulating factor (M-CSF), granulocyte-monocyte colony stimulating factor (GM-CSF), and lymphotoxini (LT) such as TNF-$\alpha$ and TNF-$\beta$.

Without inflammation, wounds and infections would never heal. Similarly, progressive destruction of the tissue would compromise the survival of the organism. However, chronic inflammation can also lead to a host of diseases, such as hay fever, periodontitis, atherosclerosis, and rheumatoid arthritis. It is for that reason that inflammation is normally closely regulated by the body.

Typically, antibiotics, non-steroidal anti-inflammation drugs (NSAIDs), and anti-histamine drugs are used to treat inflammation and they improve symptoms. However, side effects are also reported.

(2) Gout is a medical condition usually characterized by recurrent attacks of acute inflammatory arthritis, e.g., a red, tender, hot, swollen joint. Goat can be hypercuricemia, recurrent acute monoarthrities, and tophi. Gouty nephropathy is the symptom of serious goat. The metatarsal-phalangeal joint at the base of the big toe is the most commonly affected. However, it may also present as tophi, kidney stones, or urate nephropathy. It is caused by elevated levels of uric acid in the blood which crystallize and are deposited in joints, tendons, and surrounding tissues.

Hypercuricemia is the main cause of gout. About 5-18.8% patients suffering hypercuricemia may have gout in the end period. It is fatal in some cases.

Uricase differential spectrophotometric method can be used to cure hyperuricemia. Hyperuricemia is a level of uric acid in the blood that is abnormally high. In humans, the upper end of the normal range is 360 µmol/L (6 mg/dL) for women and 400 µmol/L (6.8 mg/dL) for men. Many factors contribute to hyperuricemia including genetics, insulin resistance, hypertension, renal insufficiency, obesity, diet, use of diuretics, and consumption of alcoholic beverages.

Hyperuricemia has four stages including asymptomatic hyperuricemia, acute gouty arthritis, inter-critical gout, and chronic tophaceous gout.

Diagnosis is confirmed clinically by the visualization of the characteristic crystals (e.g., monosodium urate crystal) in joint fluid. Shown negative birefringent means gout symptom. Other parts of a patient including toes, feet, and ankles can be also observed for gout symptom.

Treatment with steroids or colchicine improves gout symptoms. Once the acute attack has subsided, levels of uric acid are usually lowered via lifestyle changes, and in those with frequent attacks allopurinol or probenecid provide long-term prevention.

Precipitation of uric acid crystals, and conversely their dissolution, is known to be dependent on the concentration of uric acid in solution, pH, sodium concentration, and temperature. Established treatments address these parameters.

Uricosuric agents are substances that increase the excretion of uric acid in the urine, thus reducing the concentration of uric acid in blood plasma. In general, this effect is achieved by action on the proximal tubule. Drugs that reduce blood uric acid are not all uricosurics. Blood uric acid can be reduced by administered uricosuric agents for seven to ten days gradually increased in amount. Other drugs such as probenecid and benzbromarone can also be used.

Treatment with xanthine oxidase inhibitor, allopurinol, hypoxanthine, and xanthine oxidase improves symptoms. Also, mercaptopurine or azathioprine can be used to treat gout but caution should be taken due to its side effects.

(3) Wound healing is an intricate process in which the skin repairs itself after injury. In normal skin, the epidermis (i.e., outermost layer) and dermis (i.e., inner or deeper layer) exists in a steady-state equilibrium, forming a protective barrier against the external environment. Once the protective barrier is broken, the normal process of wound healing is immediately set in motion. The classic model of wound healing is divided into four sequential phases: hemostasis, inflammatory, proliferative, and remodeling. Upon injury to the skin, a set of complex biochemical events takes place in a closely orchestrated cascade to repair the damage. Within minutes post-injury, platelets aggregate at the injury site to form a fibrin clot. This clot acts to control active bleeding.

Growth factors related to wound healing include fibroblast growth factor 2 (FGF2), platelet-derived growth factor (PDFG), epidermal growth factor (EFG), keratinocyte growth factor (KGF), transforming growth factor-$\alpha$ (TGF-$\alpha$), transforming growth factor-$\beta$ (TGF-$\beta$), and vascular endothelial growth factor (VEGF). These growth factors including PDFG, EFG, TGF-$\beta$, and VEFG are secreted by cells. Further, PDGF can absorb macrophages and fibroblasts and facilitates matrix protein growth. EGF can autocrine for growth. TGF-$\beta$ can facilitate fibroblasts growth. VEGF can facilitate proangiogenic matrix growth and accelerate monocyte movement. These factors are closely related to wound healing.

In the inflammatory phase, bacteria and debris are phagocytosed and removed, and factors are released that cause the migration and division of cells involved in the proliferative phase. The proliferative phase is characterized by angiogenesis, collagen deposition, granulation tissue formation, epithelialization, and wound contraction. In angiogenesis, new blood vessels are formed by vascular endothelial cells. In fibroplasia and granulation tissue formation, fibroblasts grow and form a new, provisional extracellular matrix by excreting collagen and fibronectin.

The invention discussed below is novel and nonobvious as far as the present inventor is aware.

SUMMARY OF THE INVENTION

It is therefore one object of the invention to provide an extraction method comprising the steps of (1) choosing an extraction solvent; (2) heating the extraction solvent to a first predetermined temperature; (3) adding pulverized longan seed to the extraction solvent to prepare a solution; (4) maintaining the solution at a second temperature for a predetermined period of time to obtain an extracted substance; (5) filtering the extracted substance; and (6) drying and cooling the filtered extracted substance to produce an extract.

In a first aspect of the invention, the extraction solvent is either water or inorganic compound.

In a second aspect of the invention, the inorganic compound is a solvent having a predetermined volume concentration of ethanol.

In a third aspect of the invention, the predetermined volume concentration of ethanol is about 20-95%.

In a fourth aspect of the invention, the first predetermined temperature is about 70-90° C.

In a fifth aspect of the invention, the second predetermined temperature is about 70-90° C.

In a sixth aspect of the invention, the predetermined period of time is about 1-3 hours.

In a seventh aspect of the invention, the extract comprises corilagin, ellagic acid, and gallic acid.

In an eighth aspect of the invention, the longan seed extraction can cure inflammation.

In a ninth aspect of the invention, the longan seed extraction can cure hyperuricemia.

In a tenth aspect of the invention, the longan seed extraction can heal wound.

In an eleventh aspect of the invention, the longan seed extraction can inhibit microorganism growth.

In a twelfth aspect of the invention, the longan seed extraction has the following advantages including curing inflammation, curing hyperuricemia, healing wound, and inhibiting microorganism growth.

The above and other objects, features and advantages of the invention will become apparent from the following detailed description taken with the accompanying drawings.

BRIEF DESCRIPTION OF THE DRAWINGS

FIG. 1B is a table showing conditions of operating the HPLC apparatus;

FIG. 5B is a table showing results of anti-gout experiment with respect to xanthine oxidase and other samples;

FIG. 10 is a table showing results of growth factors when subjecting to crystal violet dyeing method by using different doses; and FIG. 11 is a table showing results when subjecting to ELISA test.

DETAILED DESCRIPTION OF THE INVENTION

Referring to FIGS. 1 to 11, a method of making longan seed extract in accordance with the invention comprises the following steps:

(a) An extraction solvent such as water or inorganic compound is chosen. In this embodiment, a solvent having 20-95% of ethanol is chosen as the extraction solvent.

(b) The extraction solvent is heated to a temperature of about 70-90° C.

(c) Pulverized longan seed is added to the extraction solvent to prepare a solution.

(d) The solution is maintained at a temperature of about 70-90° C. for about 1 to 3 hours for extraction.

(e) The extracted substance is filtered.

(f) The filtered extracted substance is dried at a low temperature and low atmospheric pressure environment.

(g) Finally, longan seed extract is obtained.

Figure 1:
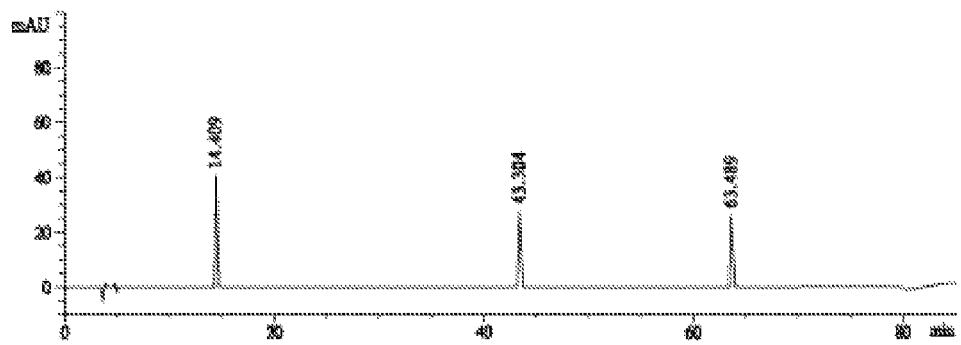
FIG. 1 is a chart of results obtained by processing a solution comprising gallic acid, corilagin, and ellagic acid chosen as a control group according to the invention by means of an HPLC apparatus.
Figure 1A:
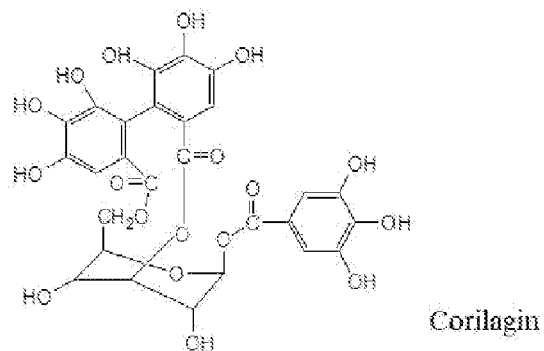
FIG. 1A shows the structural formulas of corilagin, gallic acid, and ellagic acid.
Figure 1A:
Figure 1A:
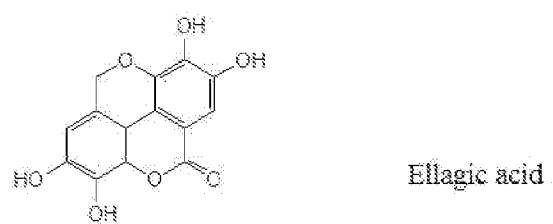

Above steps of the invention are done in a high performance liquid chromatography (HPLC) apparatus. The extract is comprised of gallic acid, corilagin, and ellagic acid. The structural formulas of gallic acid, corilagin, and ellagic acid are shown in FIG. 1A. Further, equipment and conditions of the HPLC apparatus are shown in FIG. 1B.

Figures 2, 2A:
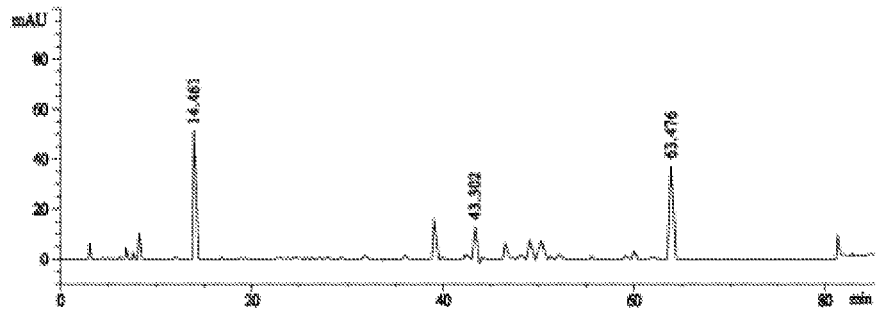
FIG. 2 is a graph of results obtained by processing a longan seed extract comprising gallic acid, corilagin, and ellagic acid chosen as a control group according to the invention by means of an HPLC apparatus.
FIG. 2A is a table showing results of original IL-1β and after stress IL-1β in the anti-inflammation test.
Figures 3, 3A:
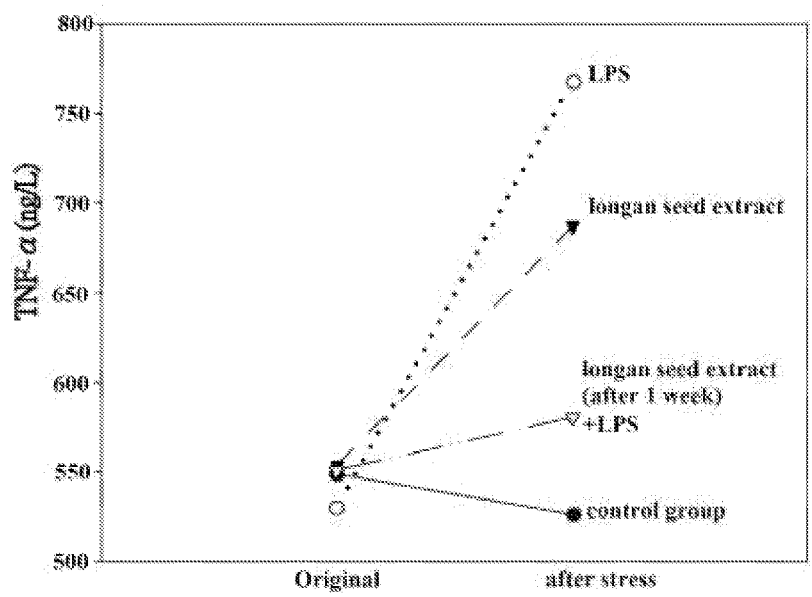
FIG. 3 plots TNF-α versus IL-1β for LPS, longan seed extract, longan seed extract after one-week, and control group.
FIG. 3A is a table showing results of original TNF-α and after stress TNF-α in the anti-inflammation test.

The solution comprising gallic acid, corilagin, and ellagic acid is chosen as a control group. The solution is processed by the HPLC apparatus and its results are shown in FIG. 1. Retention time of gallic acid of 42.42 μg/ml is 14.409 minutes, retention time of corilagin of 52.72 μg/ml is 43.304 minutes, and retention time of ellagic acid of 22.4 μg/ml is 63.489 minutes respectively. The longan seed extract is processed by the HPLC apparatus and its results are shown in FIG. 2. Peaks of the longan seed extract have retention time of 14.461, 43.302, and 63.476 minutes respectively. Contents of the longan seed extract are the same as that of the solution (i.e., gallic acid, corilagin, and ellagic acid).

Symptoms improvements by treating with the longan seed extract of the invention are discussed in the following experiments:

Experiment 1

Treatments with longan seed extract obtained from a solvent having 50% of ethanol, longan seed extract A obtained from a solvent having 100% pure water, and longan seed extract obtained from a solvent having 20% of ethanol improve inflammation symptoms as discussed below.

24 Sprague Dawley (SD) rats are grouped into nine groups of different SD rats in which one group is chosen as control group and the remaining groups chosen as treatment groups. It is noted that all SD rats are male in the invention. Each SD rat has a weight of 200-250 g. Room temperature is kept at 23° C. Room is kept bright for 12-hour and dark for next 12-hour repeatedly. Water is treated by reverse osmosis.

SD rats in the control group is fed with water only.

Longan seed extract is oral fed to the SD rats of a first treatment group in the weight of 0.5 g/Kg of SD rat. After one week, LPS (lipopolysaccharides) of 2.5 mg/Kg of SD rat is abdomen injected into each SD rat. Another one day is waited.

Longan seed extract is oral fed to each SD rat of a second treatment group in the weight of 0.5 g/Kg of SD rat, waiting for one week, LPS of 2.5 mg/Kg of SD rat is abdomen injected into each SD rat, and waiting for 48 hours.

LPS of 2.5 mg/Kg of SD rat is abdomen injected into each SD rat of a third treatment group, waiting for 24 hours, and oral feeding longan seed extract A of 0.5 g/Kg of SD rat to each SD rat.

LPS of 2.5 mg/Kg of SD rat is abdomen injected into each SD rat of a fourth treatment group, waiting for 24 hours, and oral feeding longan seed extract B of 0.5 g/Kg of SD rat to each SD rat.

LPS of 2.5 mg/Kg of SD rat is abdomen injected into each SD rat of a fifth treatment group, waiting for 24 hours, and oral feeding longan seed extract of 0.5 g/Kg of SD rat to each SD.

LPS of 2.5 mg/Kg of SD rat is abdomen injected into each SD rat of a sixth treatment group, waiting for 48 hours, and oral feeding longan seed extract of 0.5 g/Kg of SD rat to each SD rat.

LPS of 2.5 mg/Kg of SD rat is abdomen injected into each SD rat of a seventh treatment group, and waiting for 24 hours.

Oral feeding longan seed extract of 0.5 g/Kg of SD rat to each SD rat of an eight treatment group.

After one night of abstaining from food and drink, ether as anesthesia agent is administered to each SD rat. Next, serum from arterial blood of the SD rat is withdrawn for check by using an Enzyme-linked immunosorbent assay (ELISA) test. It is noted that data obtained by the experiment is subject to ANOVA (one-way analysis of variance).

As shown in columns "IL-1β (ng/L) original" and "IL-1β (ng/L) after stress" of FIG. 2A, oral feeding of longan seed extract and abdomen injection of LPS can enhance the immune system of the SD rats. As shown in columns "TNF-α (ng/L) original" and "TNF-α (ng/L) after stress" of FIG. 3A and FIG. 3, oral feeding of longan seed extract and subsequent abdomen injection of LPS as well as only oral feeding of longan seed extract can enhance the capability of resisting inflammation of the SD rats.

Experiment 2

Treatments with longan seed extract obtained from a solvent having 50% of ethanol improve gout symptoms as discussed below.

24 SD rats are grouped into three groups of eight SD rats in which first group is chosen as control group, second group chosen as treatment group, and third group chosen as longan seed group. Each SD rat has a weight of 200-250 g. Room temperature is kept at 23° C. Room is kept bright for 12-hour and dark for next 12-hour repeatedly. Water is treated by reverse osmosis.

SD rats in the control group is fed with water only.

Hypoxathine in the weight of 300 mg/Kg of SD rat and oxonic acid in the weight of 250 mg/Kg of SD rat are oral fed to the SD rats of the treatment group. Hypoxathine in the weight of 300 mg/Kg of SD rat, oxonic acid in the weight of 250 mg/Kg of SD rat, and longan seed of 0.1 wt % are oral fed to the SD rats of the longan seed group.

After one night of abstaining from food and drink, ether as anesthesia agent is administered to each SD rat. Next, serum from arterial blood of the SD rat is withdrawn for checking blood concentrations of uric acid by using Ciba-cornint 550. It is noted that data obtained by the experiment is subject to ANOVA.

Figures 4, 4A:
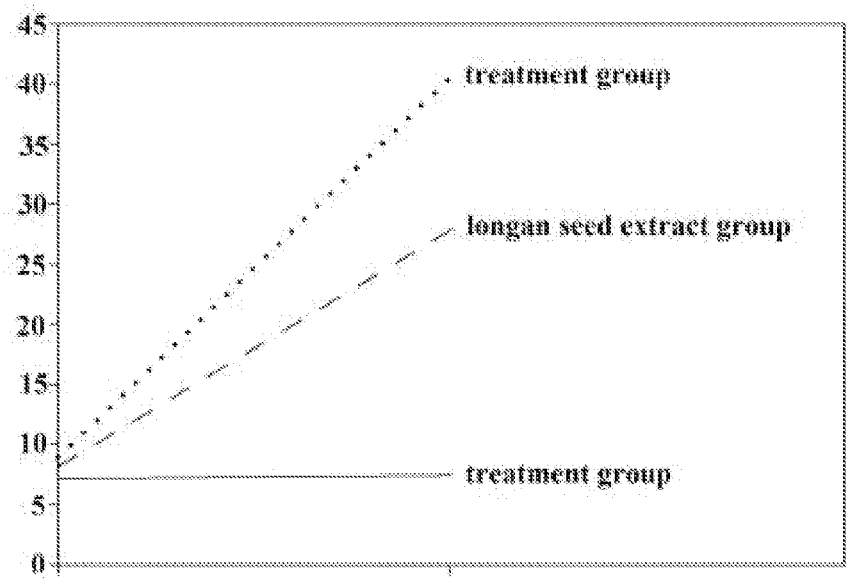
FIG. 4 plots the effect of decreasing serum of SD rats for treatment group, longan seed extract group, and control group.
FIG. 4A is a table of uric acid concentrations of control group, treatment group and longan seed extract group for anti-gout experiment.

As shown in FIGS. 4 and 4A, longan seed extract obtained from a solvent having 50% of ethanol lower about 32% of blood concentrations of uric acid of SD rats.

Experiment 3

50 μmol/L of xanthine is prepared by using a buffer solution called PBS (phosphate buffered saline). 0.1-0.2 unit/ml of xanthine oxidase is prepared by using PBS. Following samples are prepared: (1) Preparation of pure water and preparation of longan seed extract therefrom. (2) Preparation of solution having 20% ethanol and preparation of longan seed extract therefrom. (3) Preparation of solution having 50% ethanol and preparation of longan seed extract therefrom. (4) Preparation of solution having 95% ethanol and preparation of longan seed extract therefrom. Allopurinol is taken as a positive control group. Xanthine oxidase is added to the control group. After five minutes, xanthine is added to the control group. Water is added to a blank control group. Xanthinie oxidase is added to each sample. After five minutes, xanthine is added to each sample. A spectrometer is used to emit light of wavelength of 290 nm to impinge on the samples and the control groups. Light absorption change is measured every 20-second for five minutes. Finally, enzyme activity is calculated. Xanthine oxidase inhibition ratio is defined by 1 minus enzyme activity of treatment group divided by enzyme activity of control group. As shown in FIG. 5B, a maximum of 60% xanthine oxidase inhibition ratio can be obtained.

Experiment 4

Gout toxicity elimination is tested below. Material is longan seed extract.

In an acute toxicity test, there are two groups each having 8-10 SD rats. Food is abstained from the groups but water is not abstained for one night. Oral feeding longan seed extract of 1 g/kg and 3 g/kg, and de-ionized water 1 ml/100 g to each SD rat for 28 consecutive days in which observing weight of each SD rat twice per day and weight of each SD rat is measured once per week. Thereafter, food is abstained from the SD rats for one night. Ether as anesthesia agent is administered to each SD rat. Next, serum from arterial blood of the SD rat is withdrawn for checking GOT, GPT (Glutamate Pyruvate Transaminase), albumin, globulin, and greatinine by using Ciba-cornint 550. It is noted that data obtained by the experiment is subject to ANOVA. Further, Dunnett check is conducted with value P less than 0.01 as great improvement.

Results are discussed below.

Acute toxicity test aims at obtaining a maximum sample in one administration that causes deaths of half of the tested animals. 1.0 ml/100 g of SD rat and 450 mg/ml concentration are the maximum amount per sample. 15 g/kg is the standard sample. Longan seed extract of 15 g/kg is administered to each of ten SD rats. Observation for 14 days. No deaths occur. Sample of LD50 is greater than 15 g/kg causing deaths of half of the SD rats. No significant differences are observed between SD rats of the control group and that of the treatment group after 14 days.

28-day toxicity test aims at finding a sample that causes death of half SD rats. Further, one-fifth of the sample is taken as a maximum sample. 3 g/kg and 1 g/kg are taken as the maximum samples. Two treatment groups each have 8-1 SD rats. Oral feeding 3 g/kg of longan seed extract to SD rats of one treatment group and oral feeding 1 g/kg of longan seed extract to SD rats of the other treatment group are performed for 28 consecutive days. Thereafter, no deaths are found and there are no significant weight differences between the SD rats of treatment groups and the SD rats of a control group.

Figures 6, 6A:
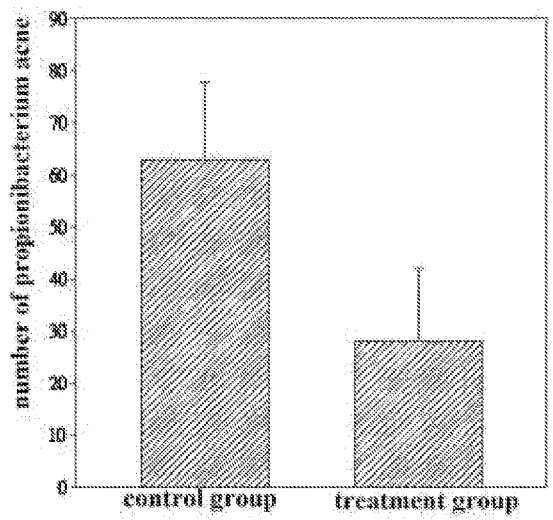
FIG. 6 plots the number of *propionibacterium acne* for control group and treatment group.
FIG. 6A is a table showing results of toxicity test by subjecting to consecutive oral feeding.

Serum from arterial blood of the SD rats of the treatment groups is withdrawn for check. As shown in FIG. 6A, there are no significant serum composition differences between the SD rats of treatment groups and the SD rats of a control group. Further, there are no significant weight differences of the liver and the kidneys between the SD rats of treatment groups and the SD rats of a control group. It is concluded that the administration of longan seed extract does not affect weight of organs of an SD rat, organs such as heart, liver, kidneys, testes, etc. of the SD rats of treatment groups functions normally, and no adverse effects to SD rats is confirmed.

Experiment 5

This is a sterilization experiment. Materials include 2.5 mg/ml of longan seed extract. A solution is made y adding water (obtained by reverse osmosis) to the longan seed extract. The solution is next filtered by a mini pore to produce a sterilized PBS.

*Escherichia coli* and *Staphylococcus aureua* are grown in an LB broth at 37° C. for 16 hours. Next, 1×PBS is used to wash the grown *Escherichia coli* and *Staphylococcus aureua* for three times in which a rotation of 3,000 rpm/minute for ten minutes is performed after each washing. A spectrometer is used to test OD value of the washed *Escherichia coli* and *Staphylococcus aureua*. Finally, *Escherichia coli* and *Staphylococcus aureua* having OD value of 0.3 is added to 1×PBS to prepare a solution which is in turn diluted with pure water to form a solution having the amount of *Escherichia coli* and *Staphylococcus aureua* 10% less than that prior to dilution. Next, the solution is reacted at 37° C. for one hour. Next, adding 5, 10, 20, 50, and 100 µl to the LB broth. Next, the solution is reacted at 37° C. for 18 hours. Next, calculate the number of *Escherichia coli* and *Staphylococcus aureua*. The solution treated with PBS is taken as treatment group and that treated with water (obtained from reverse osmosis) is taken as control group.

Figure 5:
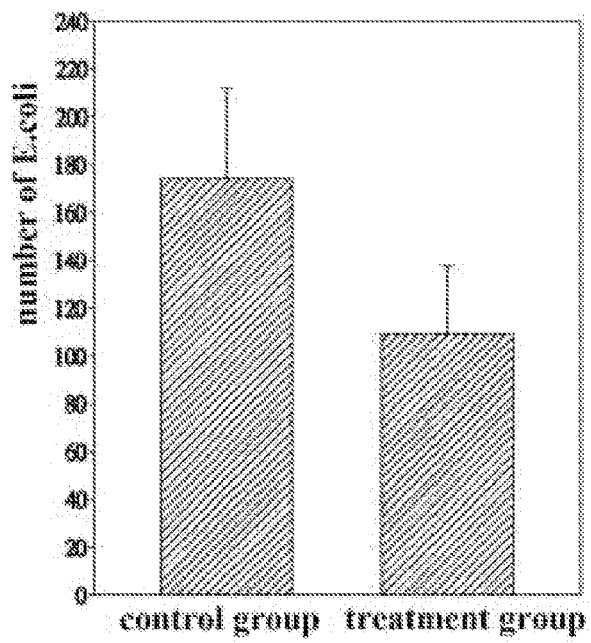
FIG. 5 plots the number of *Escherichia coli* for control group and treatment group.
Figure 5A:
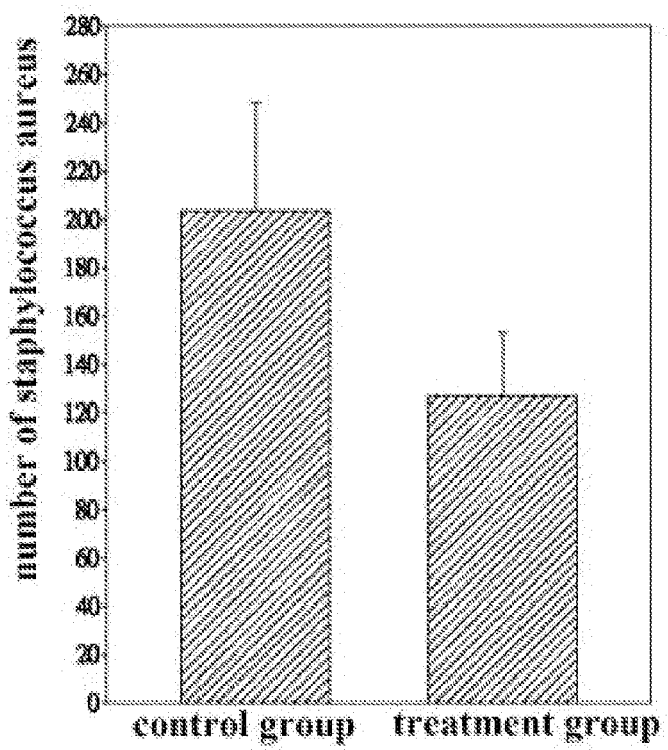
FIG. 5A plots the number of *staphylococcus aureus* for control group and treatment group.
Figures 7, 7A:
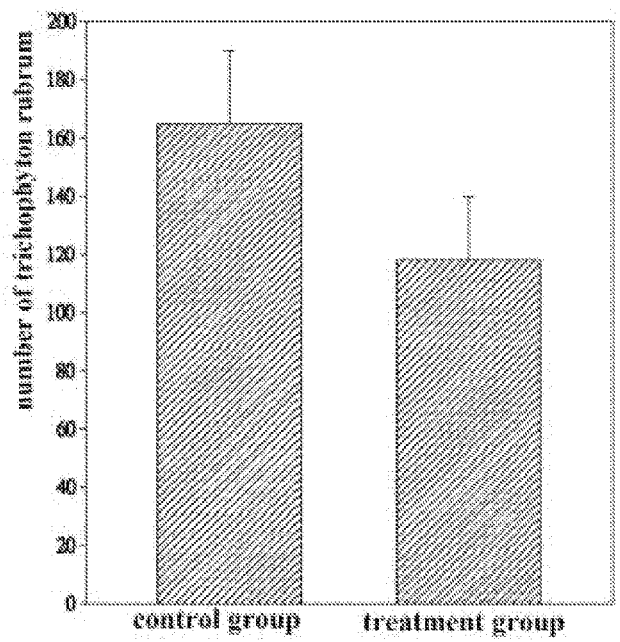
FIG. 7 plots the number of *Trichophyton rubrum* for control group and treatment group.
FIG. 7A is a table showing results of micro-organisms inhibition with respect to *Escherichia coli* and *Staphylococcus aureus*.

Above test is performed three times and results thereof are shown in FIGS. 5, 5A and 7A. It is found that the number of *Escherichia coli* and *Staphylococcus aureua* of the treatment group is greatly decrease as compared with that of the control group. It is concluded that longan seed extract has the effect of killing *Escherichia coli* and *Staphylococcus aureua*. It is useful for inhibiting acne.

Experiment 6

This is also a sterilization experiment. Above sterilized PBS is used. *Propionibacterium acne* is grown in a BAP broth at 37° C. for 48 hours. Next, 1×PBS is used to wash the grown *propionibacterium acne* for three times in which a rotation of 3,000 rpm/minute for ten minutes is performed after each washing. A spectrometer is used to test OD value of the washed *propionibacterium acne*. Finally, *propionibacterium acne* having OD value of 0.3 is added to 1×PBS to prepare a solution which is in turn diluted with pure water to form a solution having the amount of *propionibacterium acne* 10% less than that prior to dilution. Next, the solution is reacted at 37° C. for one hour. Next, adding 5, 10, 20, 50, and 100 µl to the BAP broth. Next, the solution is reacted at 37° C. for 48 hours. Next, calculate the number of *propionibacterium acne*. The solution treated with PBS is taken as treatment group and that treated with water (obtained from reverse osmosis) is taken as control group.

Figures 8, 8A:
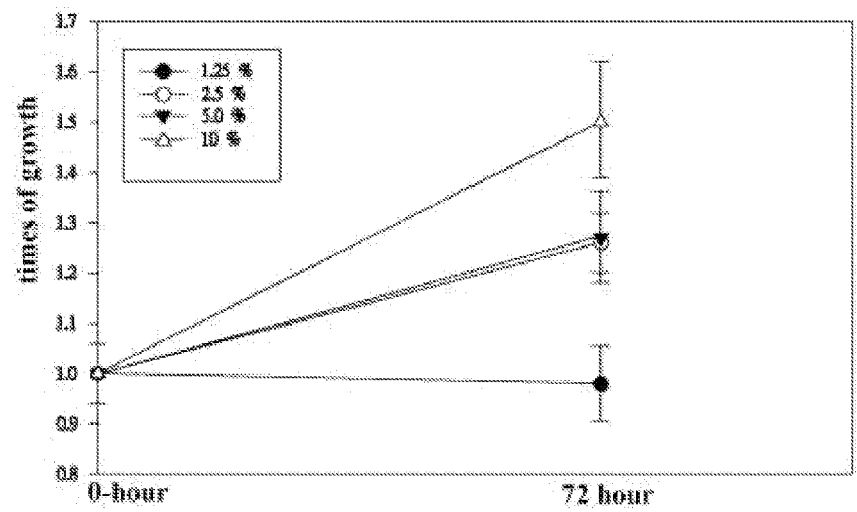
FIG. 8 plots growth times versus time for crystal violet having different dose percentages.
FIG. 8A is a table showing results of micro-organisms inhibition with respect to *propionibacterium acne*.

Above test is performed three times and results thereof are shown in FIGS. 6 and 8A. It is found that the number of *propionibacterium acne* of the treatment group is greatly decrease as compared with that of the control group. It is concluded that longan seed extract has the effect of killing *propionibacterium acne*. It is useful for inhibiting acne.

Experiment 7

This is also a sterilization experiment. Above sterilized PBS is used. *Trichopyhton rubrum* is grown in an IMA (Inhibit mold agar) broth at 30° C. for 96 hours. Next, 1×PBS is used to wash the grown *Trichopyhton rubrum* for three times in which a rotation of 3,000 rpm/minute for ten minutes is performed after each washing. A spectrometer is used to test OD value of the washed *Trichopyhton rubrum*. Finally, *Trichopyhton rubrum* having OD value of 0.1 is added to 1×PBS to prepare a solution which is in turn diluted with pure water to form a solution having the amount of *Trichopyhton rubrum* 10% less than that prior to dilution. Next, the solution is reacted at 30° C. for one hour. Next, adding 5, 10, 20, 50, and 100 µl to the IMA broth. Next, the solution is reacted at 30° C. for 96 hours. Next, calculate the number of *Trichopyhton rubrum*. The solution treated with PBS is taken as treatment group and that treated with water (obtained from reverse osmosis) is taken as control group.

Figures 9, 9A:
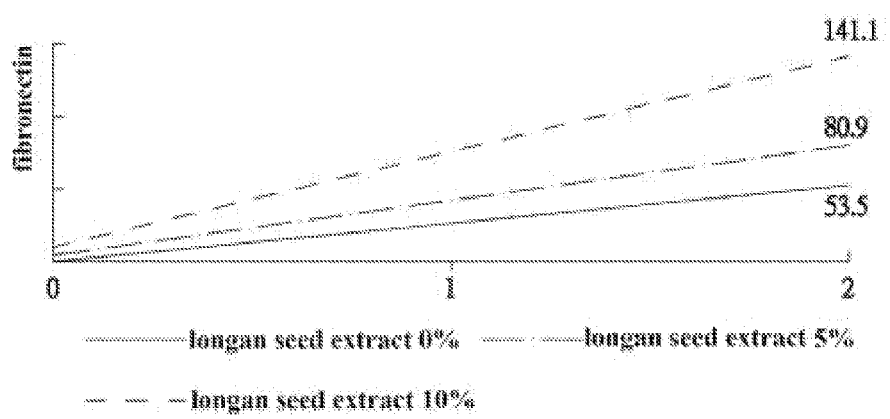
FIG. 9 plots FN for 0% longan seed extract, 5% longan seed extract, and 10% longan seed extract.
FIG. 9A is a table showing results of micro-organisms inhibition with respect to *Trichophyton rubrum*.

Above test is performed three times and results thereof are shown in FIGS. 9 and 9A. It is found that the number of *Trichopyhton rubrum* of the treatment group is greatly decrease as compared with that of the control group. It is concluded that longan seed extract has the effect of killing *Trichopyhton rubrum*. It is useful for inhibiting athlete's foot.

Experiment 8

This is a wound healing experiment. Materials include solving 5 g longan seed extract in 250 ml water to make a solution. The solution is then initially filtered by a filter paper. And in turn, the solution is filtered by a filter of 0.45 µm and another filter of 0.22 µm sequentially. A solution having 0 wt % of longan seed extract, a solution having 0.25 wt % of longan seed extract, a solution having 2.5 wt % of longan seed extract, a solution having 5.0 wt % of longan seed extract, and a solution having 10.0 wt % of longan seed extract are made for growing human epidermal keratinocytes (HEKa-C005-5C) as detailed below Cells growth: $1\times10^4$ cells/ml human epidermal keratinocytes (HEKa-C005-5C) is prepared. KC (keratinocytes) and penicillin-streptomycin available from Cascade biologics, USA are grown in an incubator having 5% $CO_2$ at 37° C.

Cells grown in this stage are called first cells. KC and penicillian-streptomycin are replenished every two days until the incubator is about 80% full of grown cells. Next, adding 0.25% trypsin-EDTA (ethylenediaminetetraacetate acid) solution having 0.25% trypsin and 0.02% EDTA. Next, it is reacted at 37° C. for 5 minutes. Cells grown in this stage called second cells. Floated KC is washed with a solution having more than 10% clean water for neutralization. Next, the solution is poured into a centrifuge which is in turn rotated at 1,500 rpm for 10 minutes for removing fine solids. Next, KC and penicillian-streptomycin are used again to float cells. Next, the solution is diluted in a 1:3 ratio with water. Finally, cells are grown in an incubator having 5% $CO_2$ at 37° C. Cells grown in this stage called third cells.

Cells growth test is next performed by means of crystal violet. HEKa-C005-5C is grown for 24, 48, and 72 hours continuously. Next, a microscope is used to observe cells growth. Clean water of 200 μl is used to wash the grown cells. Next, cells are fixed for 20 minutes by a cells fixation solution. PBST of 200 μl is used to wash the grown cells twice. Adding crystal violet of 100 μl into the solution to change color in room temperature for 30 minutes. Next, clean water of 200 μl is used to wash the grown cells trice. 1% SDS (sodium dodecyl sulfate) is used to solve cells. Rotating the solution in room temperature for 1 hour. Crystal violet attached to cells are extracted. A spectrometer is used to emit light of wavelength of 595 nm to impinge on the extract in order to measure the OD value. Further, light of wavelength of 650 nm is emitted to impinge on the extract to change the OD value. Solution without longan seed extract is taken as control group to obtain growth factors.

Human epidermal keratinocytes growth factors are determined by means of ELISA. Human epidermal keratinocytes are collected. Growth factors of the collected human epidermal keratinocytes are determined by means of commercial kits. Microtitration plate of 96 well plates is chosen. Bovine serum albumin is used for inhibition. Next, PBS-Tween is used to wash the microtitration plate. Clean solution of 100 μl is add for reaction at 37° C. for two hours. Next, PBS-Tween is used to was again. Next, rabbit-anti-growth factor Ab-HRP available from Chemicon, Temmecula, Calif. is added for reaction at 37° C. for two hours. Next, it is washed again. Next, colored substrate having O-phenyldiamine is added. Next, 50 μl of 2N $H_2SO_4$ is added to stop reaction. Next, OD value at wavelength 450 nm is measured. Finally, vascular endothelial growth factor (VEGF) is determined.

Results are shown in FIGS. 8 and 10. It is found that effects of crystal violet dying method for determining growth factor can be observed by means of a microscope. It is shown that samples with 2.5%, 5.0% and 10% of dose can increase human epidermal keratinocytes growth factors more than 1.25, 1.26 and 1.50 times as compared with control group. Particularly, the sample with 10% of dose having a p-value less than 0.05 is advantageous because it means that 10% longan seed extract can greatly increase human epidermal keratinocytes growth factors.

Results obtained by means of ELISA test are shown in FIGS. 9 and 11. In the columns "CI (collagen I) (μg/ml)" and "FN (fibronectin) (pg/ml)", after adding 5% and 10% longan seed extract, VEGF is increased greatly ($p<0.05$). This means that wound treated with longan seed extract can be quickly healed.

It is envisaged by the invention that the advantages of healing inflammation, lowering uric acid, killing microorganisms, increasing human epidermal keratinocytes growth, and helping wound healing without hurting organs can be obtained.

While the invention has been described in terms of preferred embodiments, those skilled in the art will recognize that the invention can be practiced with modifications within the spirit and scope of the appended claims.

What is claimed is:

1. A method for killing *Propionibacterium* in a patient consisting of administrating to the patient a pharmaceutically effective amount of an extract of longan seed, wherein the extract of longan seed is prepared by extracting the longan seed in water only, and the microorganism is *Propionibacterium*.

2. The method according to claim 1, wherein the extracting is conducted at about 70° C. to about 90° C.

3. The method according to claim 1, wherein the longan seed is pulverized.

4. The method according to claim 1, which is for treating acne.

* * * * *